United States Patent [19]

Schaper et al.

[11] Patent Number: 4,719,042

[45] Date of Patent: Jan. 12, 1988

[54] TERTIARY ALKYL-SUBSTITUTED ALCOHOLS AS PERFUMES

[75] Inventors: Ulf-Armin Schaper, Krefeld; Siegfried Bloesl, Schwaebisch-Gmuend; Klaus Bruns, Krefeld-Traar; Benno Streschnak, Krefeld, all of Fed. Rep. of Germany

[73] Assignee: Henkel Kommanditgesellschaft auf Aktien, Duesseldorf, Fed. Rep. of Germany

[21] Appl. No.: 28,290

[22] Filed: Mar. 20, 1987

[30] Foreign Application Priority Data

Mar. 21, 1986 [DE] Fed. Rep. of Germany ....... 3609523

[51] Int. Cl.[4] ......................... A61K 7/46; C07C 31/13

[52] U.S. Cl. ....................................... 512/25; 568/840

[58] Field of Search ...................... 252/522 R; 568/840

[56] References Cited

U.S. PATENT DOCUMENTS 4,168,248 9/1979 Kulka .................................. 252/522

OTHER PUBLICATIONS

Clark et al "Chem. Abst." vol. 84 (1976) p. 65175g.

Astakhova "Chem. Abst." vol. 90 p. 12161z (1979).

Kulka "Chem. Abst." vol. 92 (1980) p. 47150p.

Gurevich et al "Chem. Abst." vol. 94 (1981) p. 102761g.

Fujioka et al "Chem. Abst." vol. 102 (1985) p. 154634w.

J. S. Jellinik, "Parfumieren von Produkten", pp. 100–101, Dr. A. H. Huthig Verlag (pub.), Heidelberg, 1976.

Young et al J.Am.Chem.Soc. 67, 321 (1945).

Whitmore et al J.Am.Chem. Soc. 55, 813 (1933).

*Primary Examiner*—Werren B. Lone

*Attorney, Agent, or Firm*—Ernest G. Szoke; Henry E. Millson, Jr.; Mark A. Greenfield

[57] ABSTRACT

The invention relates to the use as perfumes of tertiary, alkyl-substituted alcohols corresponding to the general formula

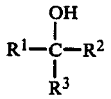

in which $R^1$ and $R^2$ are individually each a $C_{1-3}$ alkyl and $R^3$ is a $C_{4-9}$ alkyl, in compositions containing active chlorine, and to such compositions themselves.

14 Claims, No Drawings

TERTIARY ALKYL-SUBSTITUTED ALCOHOLS AS PERFUMES

BACKGROUND OF THE INVENTION

1. Field of the Invention

This invention relates to the use of certain tertiary, alkyl-substituted alcohols as perfumes in compositions containing active chlorine.

2. Statement of Related Art

In many consumer goods, for example in body-care preparations or fabric softeners, problems regarding the stability of the perfumes used are unknown. By contrast, compositions containing active chlorine, such as dish-washing detergents and/or scouring preparations and the like, destroy most perfumes so that perfuming with the desired fragrance notes is no longer possible (cf. J. S. Jellinek: "Parfumieren von Produkten", pp. 100–101, Dr. Alfred Huthig Veriag (pub.) Heldelberg, 1976). In addition, destruction of the perfumes is often accompanied by an undesirably high reduction of the active chlorine content.

DESCRIPTION OF THE INVENTION

Other than in the operating examples, or where otherwise indicated, all numbers expressing quantities of ingredients or reaction conditions used herein are to be understood as modified in all instances by the term "about".

The present invention provides methods for using certain perfumes which are stable in compositions containing active chlorine, methods for preparing such compositions, and the compositions themselves.

It has surprisingly been found that no stability problems arise where the inventive perfumes which are one or more tertiary, alkyl-substituted alcohols corresponding to the general formula

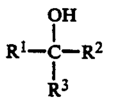

in which $R^1$ and $R^2$ are independently each a $C_{1-3}$ alkyl and $R^3$ is a $C_{4-9}$ alkyl or a mixture thereof are employed in compositions containing active chlorine, or capable of generating active chlorine upon storage, exposure to moisture or heat, etc.

The preferred species within the above formula are:
3-methylnonan-3-ol;
2-methyl-3-isopropylheptan-3-ol; and
2,3-dimethylheptan-3-ol,
all of which are included in the examples which follow.

Tertiary, alkyl-substituted alcohols corresponding to the above general formula are compounds known per se. However, their surprising stability in compositions containing or capable of generating active chlorine has hitherto remained unrecognized.

In their studies of allylic rearrangements, Young, et al [J. Am. Chem. Soc. 67, 321 (1945)], prepared various tertiary alcohols containing two isopropyl groups and one butyl or butenyl group by reaction of diisopropyl ketone with Grignard reagents. Whitmore, et al [J. Am. Chem. Soc. 55, 813 (1933)], prepared several tertiary, alkyl-substituted alcohols containing one methyl moiety and one isopropyl moiety. Furthermore, 3-methylnonan-3-ol is disclosed as a perfume in U.S. Pat. No. 4,168,248.

The tertiary, alkyl-substituted alcohols corresponding to the above general formula were used as perfumes in compositions containing active chlorine and then were subjected to a storage test. It was surprisingly found that, even after one year at room temperature, no changes in odor occurred in either liquid or solid compositions containing active chlorine and the inventive perfumes.

EXAMPLES

General Procedure for the Preparation of Tertiary, Alkyl-substituted Alcohols In a fully heated apparatus, 20 ml of a solution of 0.5 mol alkyl halide in 150 ml ether were added dropwise to 0.5 mol magnesium chips in 50 ml anhydrous ether. When the Grignard reagent began to form, the rest of the alkyl halide solution was added quickly enough so that the ether boiled gently. On completion of the addition, the mixture was stirred under reflux for about another 30 minutes.

0.45 mol of the corresponding ketone in 100 ml ether was added dropwise with stirring to the cooled Grignard solution, followed by stirring under reflux for about 30 minutes.

For working up, the reaction mixture was cooled to 0° C. and poured carefully into a cold, saturated $NH_4Cl$-solution (approx. 300 ml). The ether phase was then separated off and the aqueous phase extracted twice with 80 ml ether. The combined ethereal phases were washed with saturated sodium hydrogen carbonate and sodium chloride solution. After drying with sodium sulfate and evaporation of the solvent, the residue was distilled in vacuo.

The following compounds were prepared by this method:

(A) 3-methylnonan-3-ol prepared from ethylmethyl ketone and n-hexyl magnesium chloride
odor: flowery, similar to 2,6-dimethylheptan-2-ol.

(B) 2-methyl-3-isopropylheptan-3-ol prepared from diisopropyl ketone and n-butyl magnesium bromide
odor: damp wood, pyrethrum note.

(C) 2,3-dimethylheptan-3-ol prepared from isopropylmethyl ketone and n-butyl magnesium bromide
odor: fruity, menthone-mint note.

Typical Bouquet for Liquid and Solid Compositions Containing Active Chlorine Such as Used in Storage Tests 150 parts by weight 3-methylnonan-3-ol [PERFUME]
100 parts by weight dihydromyrcenol
150 parts by weight tetrahydrolinalool
100 parts by weight 1-cyanododecane
100 parts by weight eucalyptol
300 parts by weight dipropylene glycol
100 parts by weight terpineol The above bouquet, or one prepared with similar ingredients well known in the art, may be employed in any conventional or new composition which contains active chlorine, or is capable of releasing active chlorine upon storage and/or exposure to moisture. The formulations of such compositions do not affect the perfumes of this invention except as disclosed herein, and therefore do not form a part of this invention. The compositions may comprise any dishwashing, laundry, commercial or household detergent and/or scouring preparation, to which the perfumes of this invention are added. The amount of addition will vary with the composition ingredients, amount of free chlorine, etc. but must be in at least a perfume-effective amount. The addition may be in any order of ingredients, and may be of the perfume per se or of a conventional bouquet of the type abovementioned. There are no limitations as to physical conditions of the addition or the compositions, other than those already known in the art. The compositions with the added perfumes are considered novel.

We claim:

1. A method for perfuming a composition containing active chlorine, or capable of generating active chlorine, comprising incorporating within said composition at least a perfume-effective amount of at least one compound of the formula:

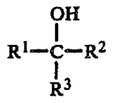

wherein:

$R^1$ and $R^2$ are independently each a $C_{1-3}$ alkyl; and $R^3$ is a $C_{4-9}$ alkyl.

2. The method of claim 1 wherein in said formula:

$R^1$ is methyl;

$R^2$ is ethyl; and $R^3$ is n-hexyl.

3. The method of claim 1 wherein in said formula $R^1$ is isopropyl;

$R^2$ is isopropyl; and $R^3$ is n-butyl.

4. The method of claim 1 wherein in said formula:

$R^1$ is methyl;

$R^2$ is isopropyl; and $R^3$ is n-butyl.

5. The method of claim 1 wherein said composition is a detergent and/or scouring preparation.

6. A perfumed composition obtained by the method of claim 1.

7. A perfumed composition obtained by the method of claim 2.

8. A perfumed composition obtained by the method of claim 3.

9. A perfumed composition obtained by the method of claim 4.

10. A perfumed composition obtained by the method of claim 5.

11. In a detergent and/or scouring composition containing active chlorine and/or which is capable of generating active chlorine, the improvement wherein a perfume-effective amount of at least one compound is added, said compound being of the formula:

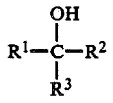

wherein:

$R^1$ and $R^2$ are independently each a $C_{1-3}$ alkyl; and $R^3$ is a $C_{4-9}$ alkyl.

12. The composition of claim 11 wherein:

$R^1$ is methyl;

$R^2$ is ethyl; and $R^3$ is n-hexyl.

13. The composition of claim 11 wherein:

$R^1$ is isopropyl;

$R^2$ is isopropyl; and $R^3$ is n-butyl.

14. The composition of claim 11 wherein:

$R^1$ is methyl;

$R^2$ is isopropyl; and $R^3$ is n-butyl.

* * * * *